(12) United States Patent
Donfried

(10) Patent No.: US 8,522,358 B2
(45) Date of Patent: Aug. 27, 2013

(54) UNIVERSAL IDENTITY SERVICE AVATAR ECOSYSTEM

(75) Inventor: Paul Andrew Donfried, Richmond, MA (US)

(73) Assignee: Verizon Patent and Licensing Inc., Basking Ridge, NJ (US)

(*) Notice: Subject to any disclaimer, the term of this patent is extended or adjusted under 35 U.S.C. 154(b) by 296 days.

(21) Appl. No.: 12/979,833

(22) Filed: Dec. 28, 2010

(65) Prior Publication Data
US 2012/0167235 A1 Jun. 28, 2012

(51) Int. Cl.
*H04N 7/16* (2006.01)

(52) U.S. Cl.
USPC ............ 726/29; 707/769; 707/E17.014

(58) Field of Classification Search
USPC ............ 726/29; 707/769, E17.014
See application file for complete search history.

(56) References Cited

U.S. PATENT DOCUMENTS

| 7,930,731 | B2* | 4/2011 | Glasgow | 726/3 |
| 2009/0157660 | A1* | 6/2009 | Jung et al. | 707/5 |
| 2009/0327219 | A1* | 12/2009 | Finn et al. | 707/3 |
| 2010/0050237 | A1* | 2/2010 | Bokor et al. | 726/4 |
| 2010/0241525 | A1* | 9/2010 | Aguera Y Arcas et al. | 705/27 |
| 2011/0119105 | A1* | 5/2011 | Grabarnik et al. | 705/7.28 |

* cited by examiner

*Primary Examiner* — Kambiz Zand
*Assistant Examiner* — Amare F Tabor

(57) ABSTRACT

A system is configured to receive personal data associated with a user, verify one or more facts from the personal data, and form an avatar based on a first subset of the received personal data, where a second, differing, subset of the received personal data is not associated with the avatar. The system is also configured to receive, from a data requester, a query including a request for the avatar, and send, to the data requester, a message that includes information associated with the avatar and an indication that the one or more facts from the personal data were verified.

17 Claims, 12 Drawing Sheets

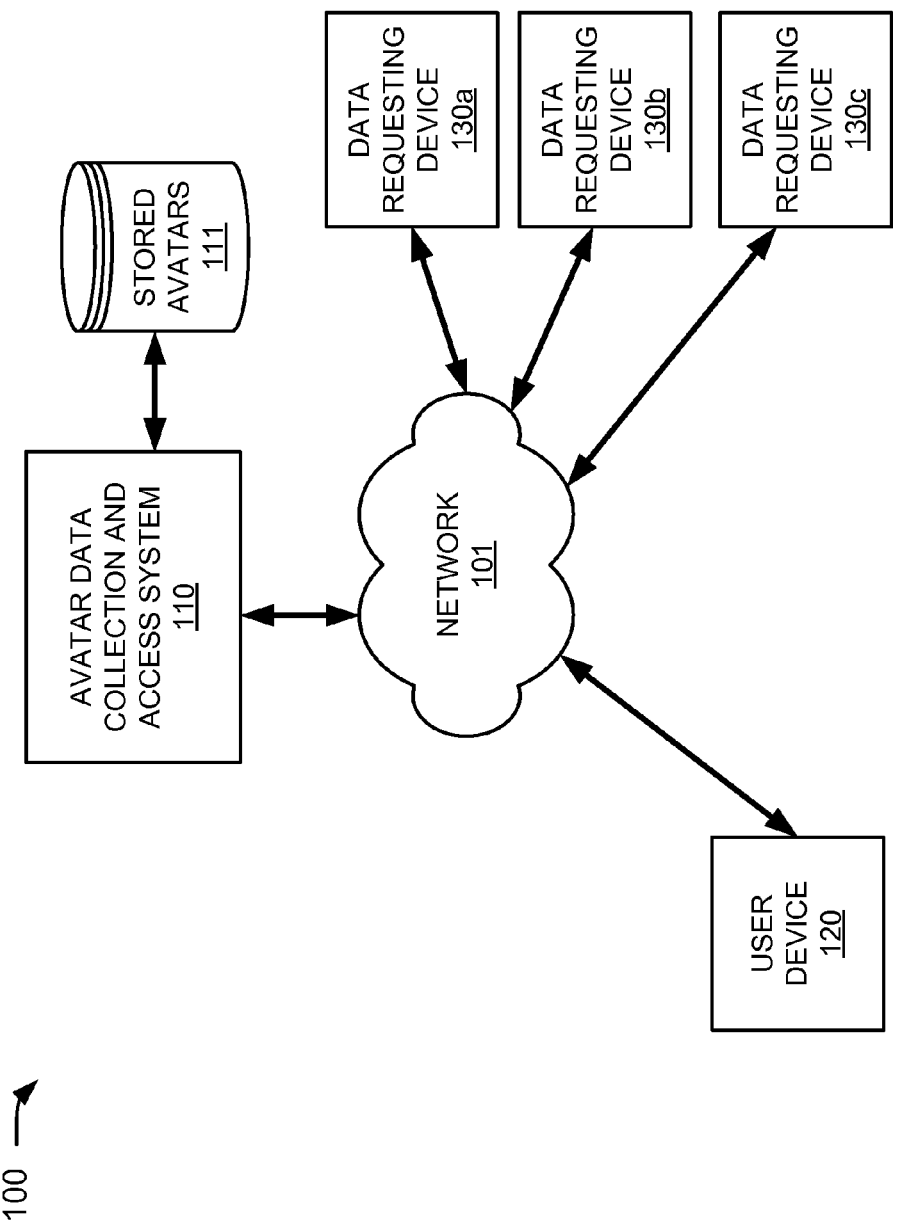

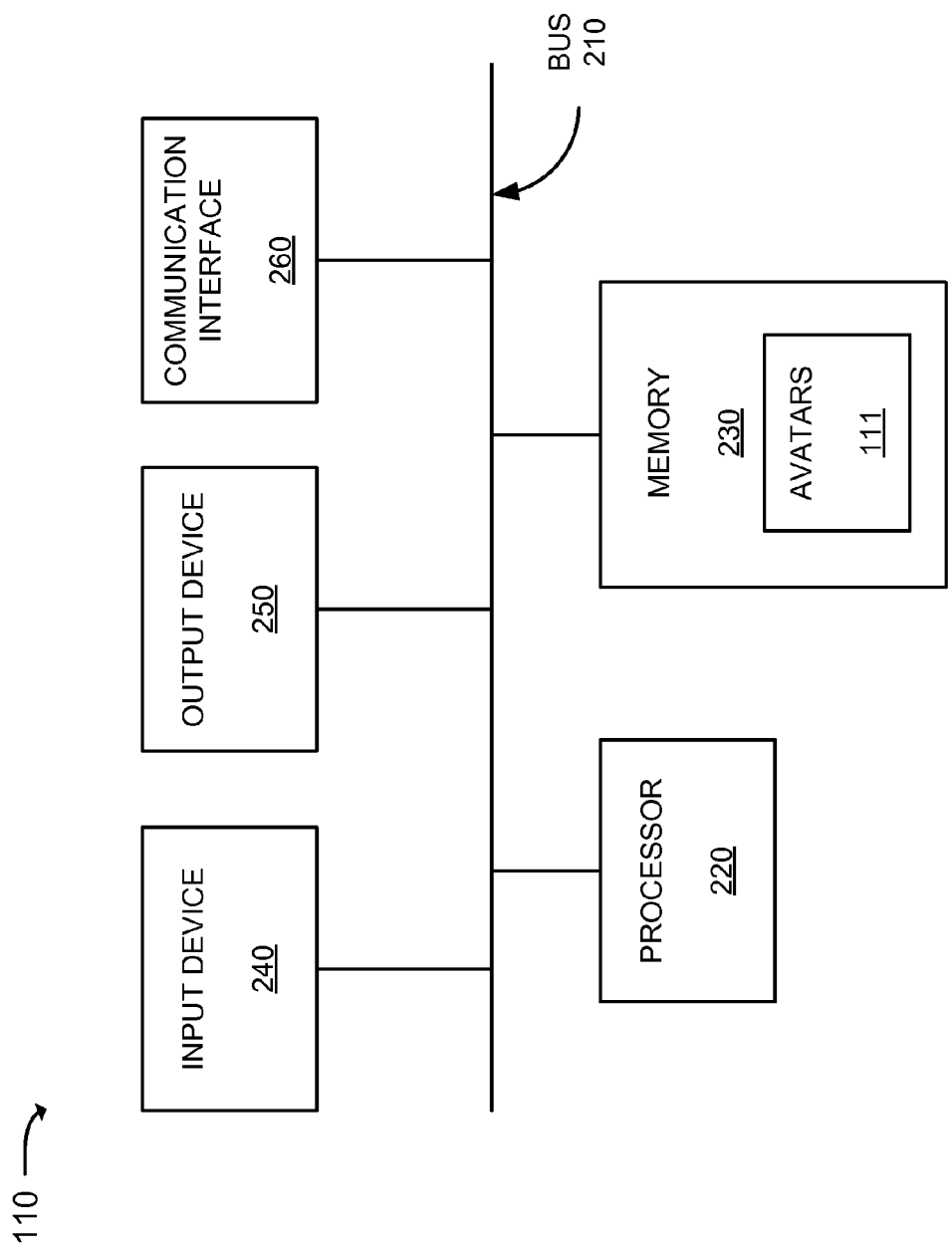

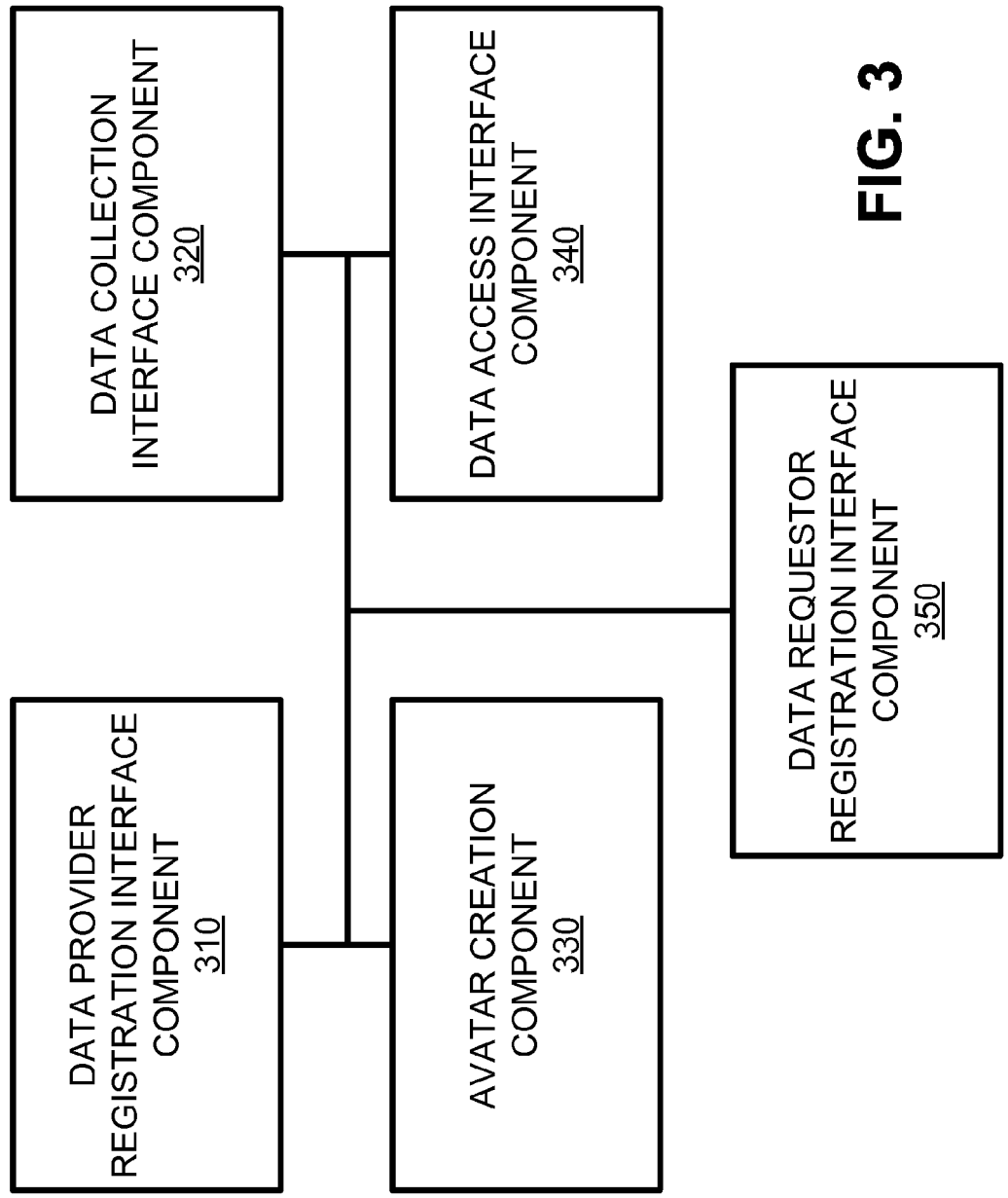

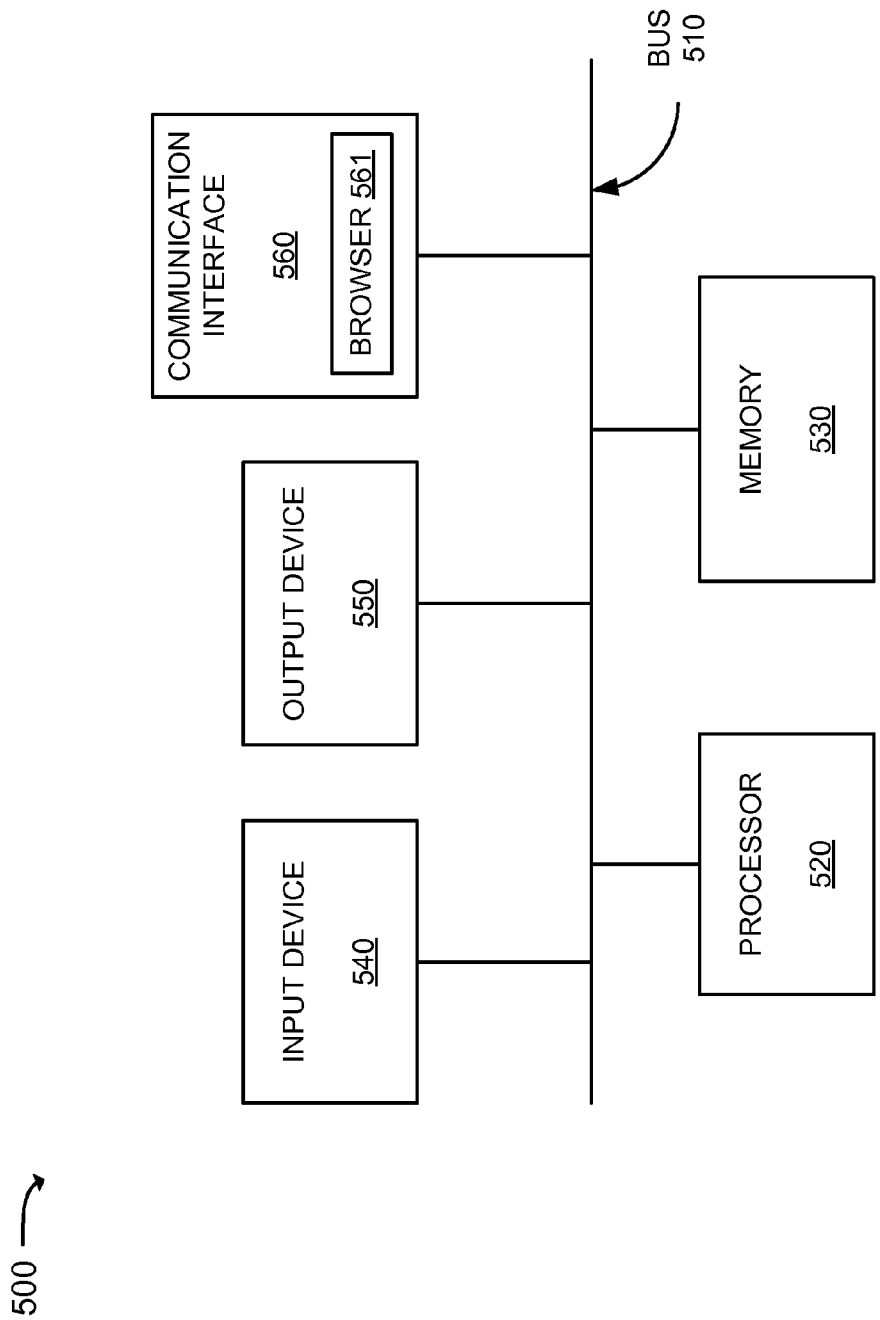

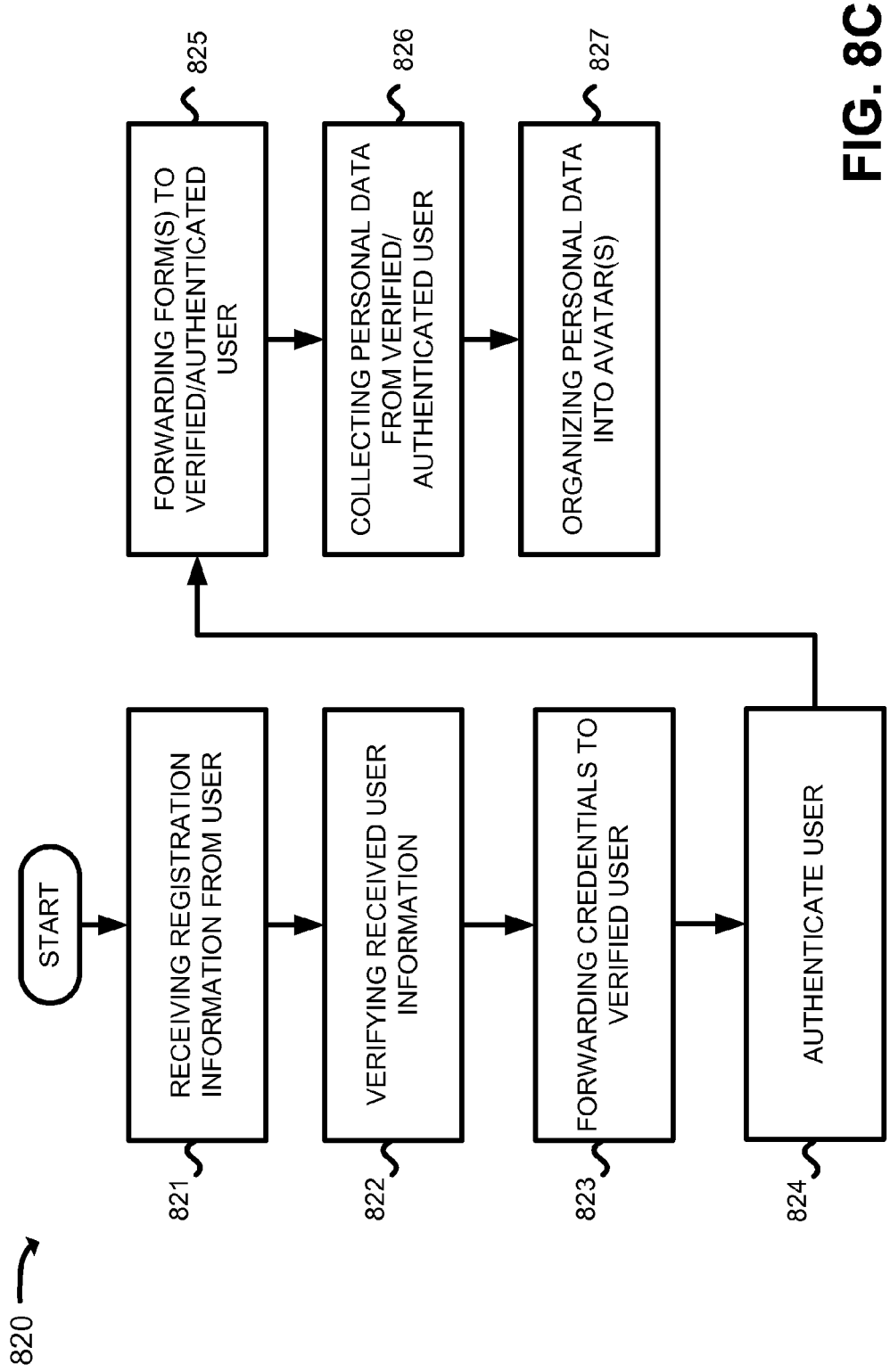

UNIVERSAL IDENTITY SERVICE AVATAR ECOSYSTEM

BACKGROUND INFORMATION

In day-to-day interactions with others, an individual typically shares various different details of that individual's personal, financial, and professional information. As part of sharing information, the individual may provide both topically relevant information and tangential information that may not be topically relevant but may be used to verify the topically relevant information. For example, to complete a commercial transaction with a vendor, an individual may provide some type of payment information, such as a credit card or checking account number. The vendor may further request, from the individual, additional information that may not be directly related to the transaction but that may be used to verify other information received for the transaction. For example, the vendor may request a user identification that may provide, for example, the individual's name, address, driver's license number, and/or other biographical information and use this additional information to authenticate the individual.

BRIEF DESCRIPTION OF THE DRAWINGS

FIG. 1 is a diagram illustrating an example of components of a system according to an implementation described herein;

FIG. 2 is a diagram illustrating example components of an avatar data collection and access system included in the system of FIG. 1 according to an implementation described herein;

FIG. 3 is a diagram illustrating example functional components of the avatar data collection and access system of FIG. 2 according to an implementation described herein;

FIG. 5 is a diagram illustrating example components of a computer device included in the system of FIG. 1 according to an implementation described herein;

FIGS. 8A-8D are flow diagrams illustrating a process for avatar-based identity management according to an implementation described herein.

DETAILED DESCRIPTION OF PREFERRED EMBODIMENTS

Figure 4A:
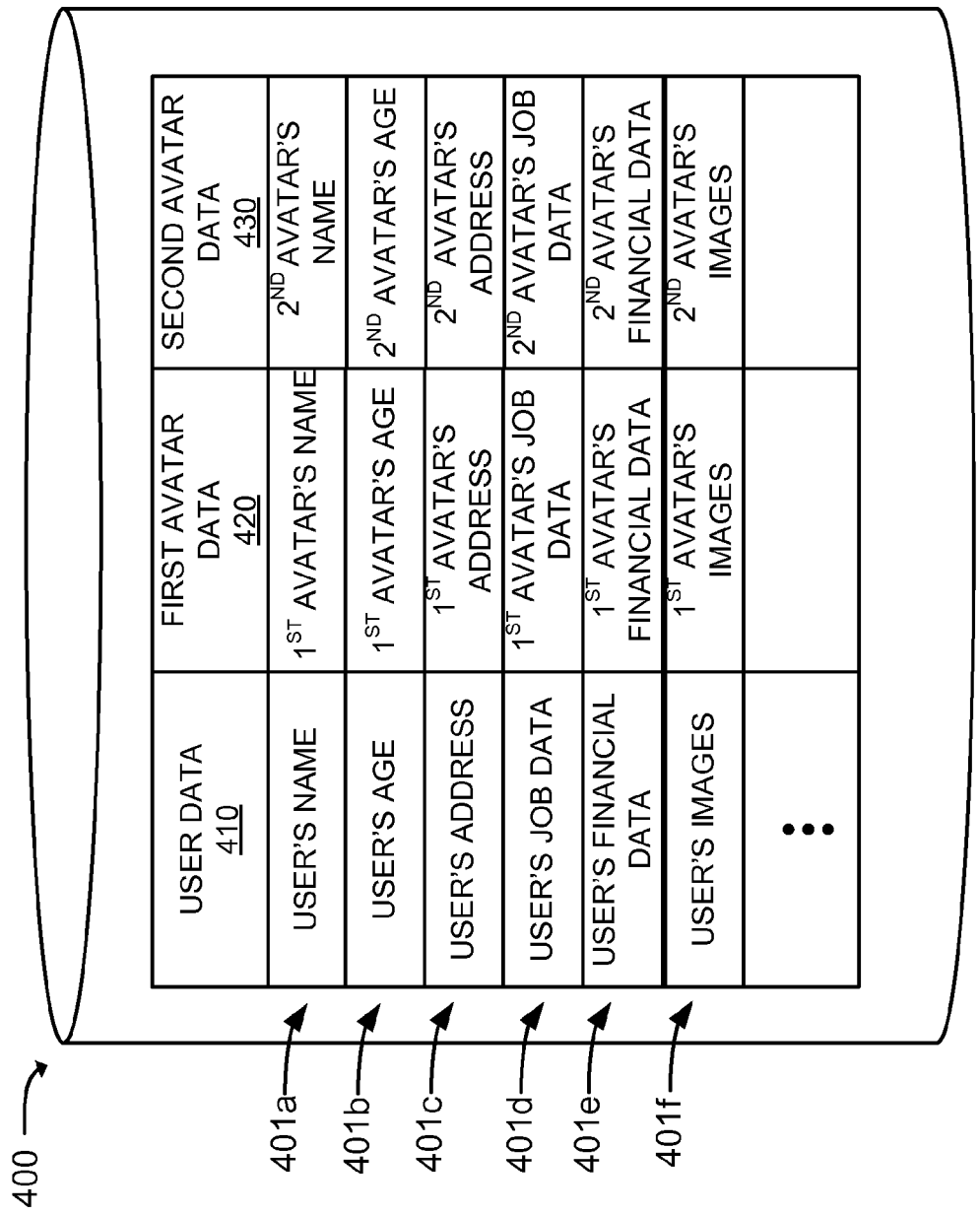
FIG. 4A is a diagram depicting examples of user data fields that may be stored by the avatar data collection and access system of FIGS. 2 and 3 according to an implementation described herein.

The following detailed description refers to the accompanying drawings. The same reference numbers in different drawings identify the same or similar elements.

An implementation, described herein, may relate to collecting a user's information, authenticating the user, and then forming one or more avatars that are based on, but differ from, the user's collected information. For example, a user may be registered, and information from that registered user may be processed to form one or more avatars. When an entity (e.g., a business, a website, etc.) requests information, that request may be processed to identify the type of requested information and one of the user's avatars may be selected according to the requested information, and information included with that selected avatar may be provided to the requesting entity.

FIG. 1 is a diagram of a system 100 according to an implementation described herein. As depicted in FIG. 1, system 100 may include avatar data collection and access system 110 that stores avatars 111, user device 120, and data requesting devices 130a-c (referred to herein collectively as "requesting devices 130" and individually as "requesting device 130"), which are connected by a network 101.

Network 101 may include a circuit-switched network and/or a packet-switched network and may enable components of system 100 to communicate with each other. For example, network 101 may include a local area network (LAN), a wide area network (WAN), a metropolitan area network (MAN), a wireless network (e.g., a Code Division Multiple Access (CDMA) network, a general packet radio service (GPRS) network, and/or a Long Term Evolution (LTE) network), an ad hoc network, a public switched telephone network (PSTN), a subset of the Internet, any other network, or any combination thereof.

Avatar data collection and access system 110 may include one or more devices (e.g., server devices) that interact with user device 120 to register a user associated with user device 120 and to receive personal information, associated with that user. For example, avatar data collection and access system 110 may receive identifying information from user device 120, authenticate user device 120 based on the identifying information, receive additional data from user device 120, and provide credentials to user device 120, once user device 120 is authenticated. As further described below, avatar data collection and access system 110 may further organize the data received from user device 120 into multiple avatars 111, with each of the avatars 111 including different subsets of the user's personal information.

Avatar data collection and access system 110 may further include one or more devices that interact with data requesting devices 130 to register respective associated users. For example, avatar data collection and access system 110 may receive identifying information from data requesting devices 130, authenticate data requesting devices 130 based on the identifying information, and provide respective credentials to authenticated data requesting devices 130. Subsequently, avatar data collection and access system 110 may classify data requesting devices 130 and provide, to data requesting devices 130, appropriate information, such as information from one or more of avatars 111, based on the classifications.

User device 120 may include any device, associated with a user, capable of exchanging messages with avatar data collection and access system 110. User device 120 may include, for example, a mobile communication device, such as a mobile phone, a personal digital assistant (PDA), or a media playing device with communication capabilities; a desktop device, such as a personal computer or a workstation; a laptop computer; a telephone terminal; or any other communication device or combinations thereof. User device 120 may receive messages from avatar data collection and access system 110 via a wired connection, a wireless connection, or a combination of a wired and a wireless connection.

User device 120 may further be capable of exchanging messages with data requesting devices 130. As part of this messaging between user device 120 and data requesting devices 130, user device 120 may authorize data requesting devices 130 to access one or more of avatars 111. For example, user device 120 may provide access credentials to data requesting devices 130 to enable data requesting devices 130 to access one or more of avatars 111 through avatar data collection and access system 110.

Each of requesting devices 130 may include one or more devices (e.g., server devices) that may exchange messages with avatar data collection and access system 110 to authenticate requesting devices 130 and to enable authenticated requesting devices 130 to access one or more of avatars 111 stored at avatar data collection and access system 110. Each of requesting devices 130 may also include one or more devices that may exchange messages with user device 120 to receive authorization, from user device 120, to access one or more of avatars 111 through avatar data collection and access system 110.

Although FIG. 1 shows example components of system 100, in other implementations, system 100 may include fewer components, different components, differently arranged components, and/or additional components than those depicted in FIG. 1. Alternatively, or additionally, one or more components of system 100 may perform one or more tasks described as being performed by one or more other components of system 100.

FIG. 2 is a diagram providing example components of avatar data collection and access system 110. As shown in FIG. 2, avatar data collection and access system 110 may include a bus 210, a processor 220, a memory 230, an input device 240, an output device 250, and a communication interface 260.

Bus 210 may permit communication among the components of avatar data collection and access system 110. Processor 220 may include one or more processors, microprocessors, and/or processing logic (e.g., application specific integrated circuits (ASICs) or field programmable gate arrays (FPGAs)) that may interpret and execute instructions.

Memory 230 may include a random access memory (RAM) or another type of dynamic storage device that stores information and instructions for execution by processor 220, a read only memory (ROM) or another type of static storage device that stores static information and instructions for processor 220, and/or some other type of magnetic or optical recording medium and its corresponding drive for storing information and/or instructions. As described in greater detail below, memory 230 may organize and store, for example, collected personal data, such as avatars 111, from information received from user devices, such as user device 110. Memory 230 may also store, for example, authentication data related to authentication of data providers, such as user device 120, and data requesters, such as data requesting devices 130.

Input device 240 may include a device that permits an operator to input information to avatar data collection and access system 110, such as a keyboard, a keypad, a button, a mouse, a pen, a microphone, one or more biometric mechanisms, and the like. Output device 250 may include a device that outputs information to the operator, such as one or more light indicators (e.g., light emitting diodes (LEDs)), a display, a speaker, etc.

Communication interface 260 may include any transceiver-like mechanism that enables avatar data collection and access system 110 to communicate with other devices and/or systems. For example, communication interface 260 may include mechanisms for communicating with other devices, such as other devices of system 100 through network 101. For example, communication interface 260 may include a modem, a network interface card, and/or a wireless interface card. Communication interface 260 may enable avatar data collection and access system 110 to interact with other devices to send forms, from memory 230, to another device, such as user device 120, receive personal information requested in the forms from the other device, and provide controlled access to the received personal information by other devices, such as data requesting devices 130.

As described herein, avatar data collection and access system 110 may perform certain operations in response to processor 220 executing software instructions included in a computer-readable medium, such as memory 230. A computer-readable medium may be defined as a non-transitory memory device. A memory device may include memory space within a single physical memory device or spread across multiple physical memory devices. The software instructions may be read into memory 230 from another computer-readable medium or from another device via communication interface 260. The software instructions included in memory 230 may cause processor 220 to perform processes described herein. Alternatively, hardwired circuitry may be used in place of or in combination with software instructions to implement processes described herein. Thus, implementations described herein are not limited to any specific combination of hardware circuitry and software.

Although FIG. 2 shows example components of avatar data collection and access system 110, in other implementations, avatar data collection and access system 110 may include fewer components, different components, differently arranged components, or additional components than depicted in FIG. 2. Alternatively, or additionally, one or more components of avatar data collection and access system 110 may perform one or more tasks described as being performed by one or more other components of avatar data collection and access system 110.

FIG. 3 is a diagram illustrating example functional components of avatar data collection and access system 110 according to an implementation described herein. In one implementation, the functions described in connection with FIG. 3 may be performed by one or more components of avatar data collection and access system 110 (FIG. 2). As shown in FIG. 3, avatar data collection and access system 110 may include data provider registration interface component 310, data collection interface component 320, avatar creation component 330, data access interface component 340, and data requester registration interface component 350.

Data provider registration interface component 310 may receive information from an individual, such as a user associated with user device 120. For example, data provider registration interface component 310 may receive information to identify the user and verify the user's identity using this identifying information. Data provider registration interface component 310 may receive this identifying information from the user or from a third-party source, as described below.

Data provider registration interface component 310 may verify the user based on the received information. Various types of verification may be used by data provider registration interface component 310 to verify the user's identifying information. For example, data provider registration interface component 310 may perform electronic verification that includes a comparison of the received information against stored information associated with the user, such as information previously received from the user or information accessed from another data source, such as a public data repository. Other known verification techniques may be employed by data provider registration interface component 310 to verify the user. For example, a user may be screened against lists of criminals.

Furthermore, data provider registration interface component 310 may provide the user with data, such as a unique encryption code or another type of credential for establishing a secure session or other connection to avatar data collection and access system 110. For example, data provider registration interface component 310 may assign a personal identification number (PIN) or, otherwise, receive an input from the user defining a PIN. In one embodiment, the data provider registration interface component 310 may provide the credential to a device associated with a registered user, such as user device 120, in the form of a cookie that operates through the associated device to identify the user to avatar data collection and access system 110.

After data provider registration interface component 310 authenticates the user, data collection interface component 320 may organize the verification information received by data provider registration interface component 310 and/or collect additional information from the authenticated user. For example, data collection interface component 320 may provide a device associated with an authenticated user, such as user device 120, with one or more forms to collect data from the user. As described below, data collection interface component 320 may receive the forms from a device associated with a data requester, such as one of data requesting devices 130. When providing the form(s) to the device associated to the authenticated user, data collection interface component 320 may pre-populate the forms with previously collected and/or stored data associated with user, such as data acquired from other forms or the information provided by the user to data provider registration interface component 310. Data collection interface component 320 may collect and store the user's responses to the forms.

Prior to accepting the data from the user, data collection interface component 320 may further authenticate a verified user, such as to request that the user provide the PIN associated with the user. Data collection interface component 320 may further strongly authenticate the user by requiring the user to provide and/or verify multiple types of personal information, such as to provide the PIN and additional personal information such as a mother's maiden name, a pet's name, a social security number, a current or prior telephone number, a driver's license number, etc.

Continuing with FIG. 3, avatar creation component 330 may organize the data, collected from the user by data provider registration interface component 310 and/or data collection interface component 320, to define one or more avatars. For purposes of the present application, an avatar may be data records that include some personal information associated with a user and additional information that differs from the user. The avatar includes sufficient information to be used a by a data requestor but differs sufficiently to protect the user's identity.

Avatar creation component 330 may associate information from the user's collected data with the avatars based, for example, on inputs from the user. For instance, the user may manually define an avatar based on an intended individual or category of individuals to receive particular information. For example, the user may define an avatar that includes sufficient information, from the user, to enable a vendor to complete online transactions. For example, this "online transaction" avatar may be associated with the user's actual payment information and shipping address, but may not include other identifying information associated with the user, such as the user's name, in order to protect the user's privacy. Because the avatar does not include the user's complete information, the vendor may not be able to directly verify and authenticate the user's payment and shipment information, but the avatar may include some type of information or code to indicate that the user is authenticated and/or that the payment and shipment information is verified. Alternatively, the avatar may be associated with sufficient personal information from the user to enable the vendor to verify other information associated with the avatar, but the avatar's information may still differ sufficiently from the user's personal information to protect the user's identity.

Avatar creation component 330 may also organize data from the authenticated user into an avatar based on information requested in a particular form. Avatar creation component 330 may also organize data, from the authenticated user, into avatars based on inputs received from a data requester, such as an entity associated with data requesting devices 130. For instance, a data requester or a form associated with the data requester may specify certain aspects of the user's information to include in an avatar and/or aspects of the user's information that may be excluded from an avatar, and avatar creation component 330 may organize the requested data to form an avatar that is specific to that data requester.

When forming an avatar, avatar creation component 330 may remove immutable personal information associated with the user, such as the user's name, address, age and/or other personal or identifying information, as appropriate. For example, avatar creation component 330 may swap information collected from one user with information collected from one or more other users. Alternatively, avatar creation component 330 may form an avatar that includes certain information associated with the user and further includes certain randomly determined information that differs from the user's information. For example, as described above, an avatar's data records may store address and payment information associated with a user, but may further store a different name, age, occupation, etc. In this way, avatar creation component 330 may form a data record associated with an avatar used for online commercial transactions that may include, for example, a user's address and credit card information but may be associated with a different name, telephone number, and age to protect the user's privacy and to provide increased security to prevent lost of the user's personal information.

Data access interface component 330 may further include, in the information associated with an avatar, an indication regarding which of the information associated with the avatar corresponds to information associated with the user. Data access interface component 330 may further include, in an avatar, an indication that the user information, included with the avatar, is reliable because the information in the avatar or other information associated with the user has been verified. Similarly, data access interface component 330 may further include, in an avatar, an indication regarding whether the user was authenticated by data collection interface component 320.

Continuing with FIG. 3, data access interface component 340 may enable an entity, such as an entity associated with data requesting device 130, to access an avatar that includes some of the personal information collected, from the data provider (e.g., user device 110), by data collection interface component 320. For example, data access interface component 340 may allow a data requester to access information associated with an avatar and may withhold user information that is not associated with the avatar. The user may direct data access interface component 340 to provide a particular avatar to a user. For example, the user may send, to data access interface component 340, instructions to associate a particular avatar with the data requester. Alternatively, the user may indirectly authorized the data requester to access the information associated with an avatar through data access interface component 340. For example, the user may provide the data requester with information, such as the avatar's name and/or some type of access code associated with the avatar, and the data requester may provide this information to data access interface component 340 to access the information associated with the avatar.

In another embodiment, data access interface component 340 may select, based on an information request by a data requester, an avatar, from multiple avatars associated with the user, to provide to the data requester. For example, data access interface component 340 may process a request from the data requester to identify particular user information associated with the request and determine an avatar that includes the identified requested user information.

In another embodiment, data access interface component 340 may select, based on a classification associated with a data requester, an avatar, from multiple avatars associated with the user, to provide to the data requester. For example, data access interface component 340 may identify and provide a particular avatar to a data requester classified as an online vendor.

Continuing with FIG. 3, data requester registration interface component 350 may receive information from a user/entity associated with one of data requesting devices 130. Data requester registration interface component 350 may authenticate the user/entity based on the received information. For example, data requester registration interface component 350 may receive information to identify the user/entity and to verify the user/entity's identity using this identifying information. Various types of authentications may be used by data requester registration interface component 350. For example, data requester registration interface component 350 may perform electronic verification of the provided information through a comparison of the received information against stored information associated with the user/entity, such as information previously received from the user/entity or information accessed from publicly available data sources. Other known authentication techniques may be employed by data requester registration interface component 350 to authenticate the user/entity.

Although FIG. 3 shows example functional components of avatar data collection and access system 110, in other implementations, avatar data collection and access system 110 may include fewer functional components, different functional components, differently arranged functional components, or additional functional components than depicted in FIG. 3. Additionally or alternatively, one or more functional components of avatar data collection and access system 110 may perform one or more tasks described as being performed by one or more other functional components of avatar data collection and access system 110.

Examples of fields in a database 400 storing the user's personal information are depicted in FIG. 4A. As depicted in FIG. 4A, data collection interface component 320 may store user data 410, first avatar data 420, and second avatar data 430. Each of user data 410, first avatar data 420, and second avatar data 430 may include one or more field 401*a-f* (referred to herein collectively as "user data fields 401" and individually as "user data field 401") to store associated information. User data fields 401 may included various information associated with a user and/or an avatar associated with the user. The example user data fields 401 depicted in FIG. 4A include, for instance, name field 401*a*, age field 401*b*, address field 401*c*, job data field 401*d*, and financial data field 401*e*. As further depicted in FIG. 4A, user data fields 401 may further store data files, such as storing images files in images data field 401*f*. However, the particular example user data fields 401, depicted in FIG. 4A, are provided merely for purposes of example and other information may be stored in user data fields 401. Additionally, or alternatively, user data fields 401 may store the actual data provided by the registered user and/or a location (i.e., a pointer or memory address) of the data.

The information stored in user data fields 401, associated with user data 410, may correspond, for example, to data provided by the registered user in response to one or more questions in forms sent from data collection interface component 320. Additionally, or alternatively, user data fields 401 may store other information associated with the user, such as information previously received from the user (such as information collected by data provided registration interface component 310) or information accessed from another data source, such as a public data repository.

The information, stored in user data fields 401 and associated with first avatar data 420 and second avatar data 430, may partially correspond to the information stored in user data fields 401 associated with user data 410. For example, avatar creation component 330 may, when creating the first avatar data 420 and the second avatar data 430, remove immutable personal information associated with the user, such as the user's name, address, age and/or other personal or identifying information, as appropriate. For example, when defining information for a user data field 401 associated with first avatar data 420 and/or second avatar data 430, avatar creation component 330 may swap information contained in a user data field 401, associated with user data 410 for one user, with corresponding information associated with another user. Alternatively, or in addition to, when defining information for user data field 401 associated with first avatar data 420 and/or second avatar data 430, avatar creation component 330 may replace information contained in a user data field 401 associated with user data 410 with randomly determined information that differs from user's data.

For example, first avatar data 420 may be defined to be provided to an online vendor and may include information in address user data field 401*c* and in financial data field 401*e* that corresponds to information associated with user data 410, but may include information in name user data field 401*a*, age user data field 401*b*, job data field 401*d*, etc. that differs from the information associated with user data 410 to protect the user's anonymity because the. First avatar data 420 and second avatar data 430 may be associated, respectively, with different subsets of user data 410 such that first avatar data 420 and second avatar data 430 may be configured for different data requesters.

The data, associated with a user data field 401 associated with first avatar data 420 and/or second avatar data 430, may include an indication of whether the data corresponds to information associated with the user, such as user data 410. Alternatively, or in addition, the data associated with a user data field 401, associated with first avatar data 420 and/or second avatar data 430, may include an indication of whether the information in this user data field 401 or other information associated with the user has been verified. Alternatively, or in addition, the data associated with a user data field 401, associated with first avatar data 420 and/or second avatar data 430, may include an indication of whether the user was authenticated by data collection interface component 320. For example, the data associated with a user field 401 may include a particular alphanumeric code or symbol.

Figure 4B:
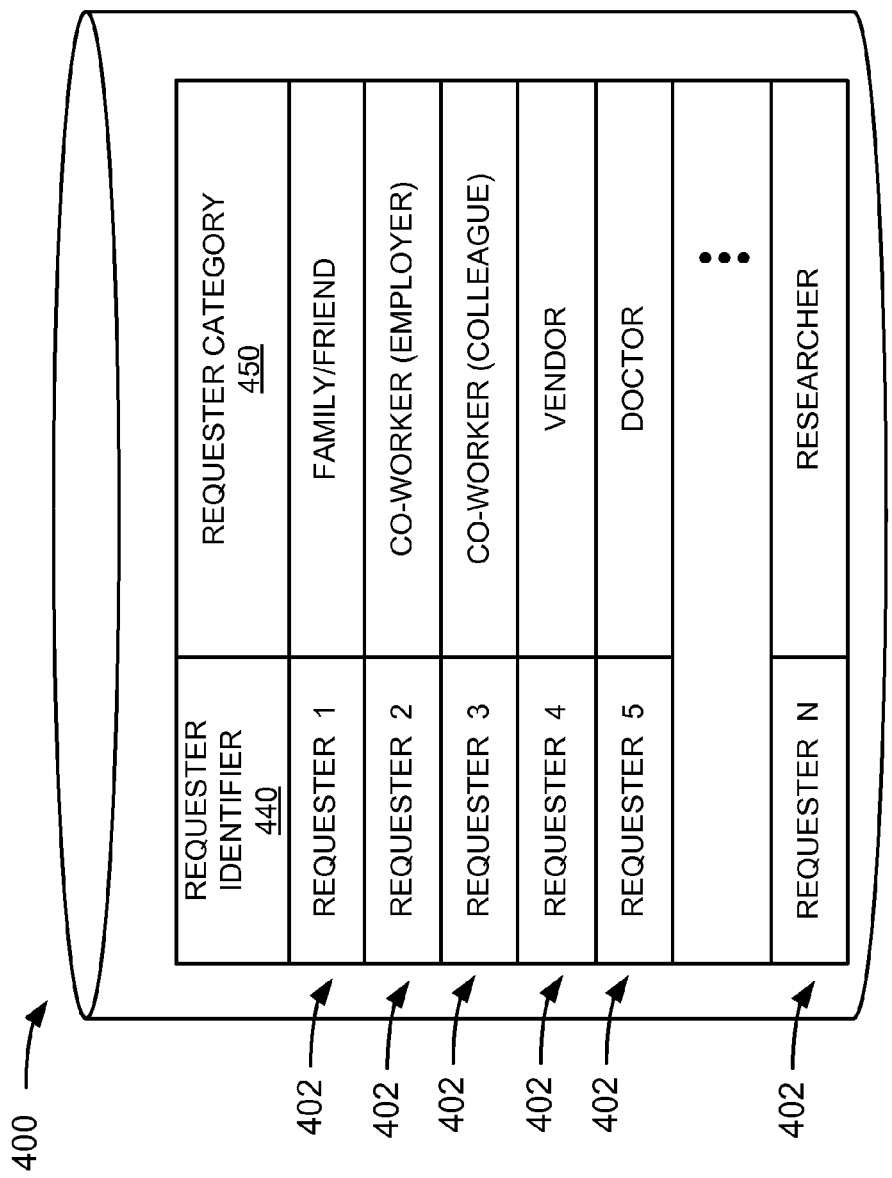
FIG. 4B a diagram depicting examples of requester data fields that may be stored by the avatar data collection and access system of FIGS. 2 and 3 according to an implementation described herein.

Database 400 may further store fields for storing records of the registered requesters. FIG. 4B depicts, for example, one or more requester data fields 402 (referred to herein collectively as "requester data fields 402" and individually as "requester data field 402") that may be stored by data requester registration interface component 350. In one implementation, requester data fields 402 may be implemented in a storage device included as part of memory 230. In other implementations, requester data fields 402 may be stored in a memory associated with another device or a group of devices, separate from or including memory 230. As shown in FIG. 4B, requester data fields 402 may include requester identification (ID) field 440 and requester category field 450.

Requester ID field 440 may store an identifier, such as an alphanumeric string that uniquely identifies a particular user or entity (e.g., an authenticated user or entity associated with one of data requesting devices 130). In FIG. 4B, requester data fields 402 are associated with requesters 1–N. It should be appreciated, however, that the particular requester data fields 402 depicted in FIG. 4B are provided solely for purposes of example, and that requester data fields 402 may be associated with any number of data requesters.

In one implementation, requester ID field 440 may store a requester ID that is derived, for example, from the data provided by a requester to data requester registration interface component 350. For example, the requester ID, stored in requester ID field 440, may be derived from a data requester's name, address, account information, telephone number, etc. The requester ID, stored in requester ID field 440, may provide an indication, for example, that two registered data requesters are related, and these relationships may be used to categorize the registered requesters. For example, data requesters sharing a contact address may be presumed to be family members or co-workers absent contrary data collected by data requester registration interface component 350.

In another implementation, the value stored in requester ID field 440 may be derived from or associated with, for example, unique encryption codes or credentials, provided by data requester registration interface component 350 to an authenticated data requester for establishing a secure session or other connection to avatar data collection and access system 110. For example, the value in requester ID field 440 may be a portion of the registered requester's encryption codes or credentials. Alternatively, the value in requester ID field 440 may be functionally-related to encryption code or credential values associated with registered data requester. For example, the registered requester may use an assigned encryption code to transmit encrypted, secure data to avatar data collection and access system 110, and avatar data collection and access system 110 may use a value stored in requester ID field 440 to decrypt the encrypted data. These particular types of values for requester ID field 440 are provided merely for purposes of example, and other types of values for requester ID field 440 may be used.

Returning to FIG. 4B, requester data field 402 may further include requester category field 450 that identifies one or more requester categories associated, by data requester registration interface component 350, with the requester associated with requester ID field 440. FIG. 4B depicts examples of requester categories that include family, friend, co-worker, vendor, doctor, and researcher categories. Each of these categories may further include sub-categories. For example, as depicted in FIG. 4B, the requester category of co-worker may include an employer (or superior) category and a colleague category. Similarly, other co-worker categories may be defined to differentiate between co-workers in different departments, offices, etc. These particular requester categories depicted in requester category field 450 are provided merely for purposes of example, and other types of requester categories may be defined, as appropriate, and stored in requester category field 450.

Although FIG. 4A shows examples of fields that may be stored in personal data record entries 401, in other implementations, user data field 401 may include fewer fields, different fields, differently arranged fields, and/or additional fields than depicted in FIG. 4A. Similarly, although FIG. 4B shows examples of fields that may be stored in requester data fields 402, in other implementations, requester data fields 402 may include fewer fields, different fields, differently arranged fields, and/or additional fields than depicted in FIG. 4B.

Database 400 may be implemented in a storage device included as part of memory 230. It should be appreciated, however, that in other implementations, database 400 may be stored in a memory associated with another device or a group of devices, separate from or including memory 230.

FIG. 5 is a diagram providing examples of components in a computer device 500 that may correspond to user device 120 or one of data requesting devices 130 described above. As shown in FIG. 5, computer device 500 may include a bus 510, a processor 520, a memory 530, an input device 540, an output device 550, and a communication interface 560.

Bus 510 may permit communication among the components of computer device 500. Processor 520 may include one or more processors, microprocessors, and/or processing logic (e.g., application specific integrated circuits (ASICs) or field programmable gate arrays (FPGAs)) that may interpret and execute instructions.

Memory 530 may include a random access memory (RAM) or another type of dynamic storage device that stores information and instructions for execution by processor 520, a read only memory (ROM) or another type of static storage device that stores static information and instructions for processor 520, and/or a type of magnetic or optical recording medium and its corresponding drive for storing information and/or instructions.

Memory 530 may store, for example, forms received from avatar data collection and access system 110 and personal data provided by a user in response to the forms. Memory 530 may also store, for example, authentication data related to authentication of computer device 500 by avatar data collection and access system 110.

Input device 540 may include a device that permits an operator to input information to computer device 500, such as a keyboard, a keypad, a mouse, a pen, a microphone, one or more biometric mechanisms, or other similar devices. Output device 550 may include a device that outputs information to the operator, such as one or more light indicators (e.g., light emitting diodes (LEDs)), a display, a speaker, etc.

Communication interface 560 may also include any transceiver-like mechanism that enables computer device 500 to communicate with other devices and/or systems. For example, communication interface 560 may include mechanisms for communicating with other devices, such as other devices of system 100 through network 101 (FIG. 1). For example, communication interface 560 may include a modem, a network interface card, and/or a wireless interface card. Communication interface 560 may enable computer device 500 to interact with other devices to receive forms and forward a user's responses to forms to another device, such as avatar data collection and access system 110, and to provide authorization to enable other devices, such as data requesting devices 130, to access to the stored personal information specified by a user associated with computer device 500.

Communications interface 560 may further include a browser 561 or another application to receive a form from data requesting devices 130, to receive a user input in response to the form, and to forward the user's inputs to avatar data collection and access system 110. Alternatively, browser 561 may enable a data requesting user to create and forward a form to avatar data collection and access system 110.

As described herein, computer device 500 may perform certain operations in response to processor 520 executing software instructions included in a computer-readable medium, such as memory 530. The software instructions may be read into memory 530 from another computer-readable medium or from another device via communication interface 560. The software instructions included in memory 530 may cause processor 520 to perform processes described herein. Alternatively, hardwired circuitry may be used in place of or in combination with software instructions to implement processes described herein. Thus, implementations described herein are not limited to any specific combination of hardware circuitry and software.

Although FIG. 5 shows examples of components of computer device 500, in other implementations, computer device 500 may include fewer components, different components, differently arranged components, or additional components than depicted in FIG. 5. Alternatively, or additionally, one or more components of computer device 500 may perform one or more tasks described as being performed by one or more other components of computer device 500.

Figure 6:
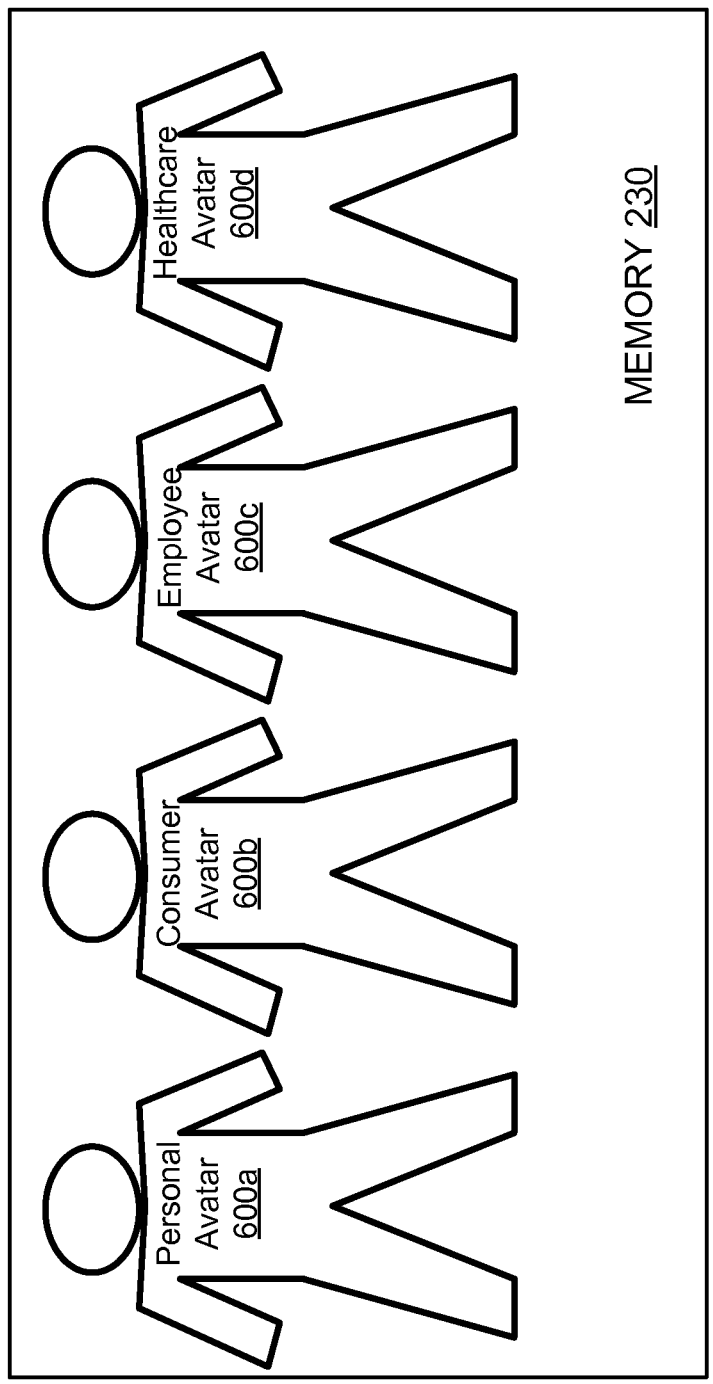
FIG. 6 is a diagram depicting examples of avatars that may be stored by the avatar data collection and access system of FIGS. 2 and 3 according to an implementation described herein.

FIG. 6 depicts examples of avatars 600a-e for a registered user that may be stored in connection with the operation of avatar creation component 330 and/or data access interface component 340. In one implementation, avatars 600a-e may be implemented in a storage device included as part of memory 230. It should be appreciated, however, that in other implementations, avatars 600a-e may be stored in a memory associated with another device or a group of devices, separate from or including memory 230. As described above, various components of avatar data collection and access system 110 may form avatars based on a user's personal data and then provide information associated with one of the avatars to a data requester.

As described above, a person (or a biological entity) may be associated with multiple avatars. As used herein, an avatar includes a set of identity attributes associated with a biological entity, with each avatar including one or more core attributes associated with the person and differing in other attributes from the person. FIG. 6 depicts that a user is associated, for example, with personal avatar 600a, consumer avatar 600b, employee avatar 600c, and healthcare avatar 600d.

Core attributes included in the personal avatar 600a may include, for example, personal information about the user, such as the name, age, and address of the user, information about the user's family, and/or other personal data, such as personal images. Personal avatar 600a may not include other information related to the user, such as the user's job and financial data. Personal avatar 600a may be shared, by data access interface component 340, with data requesters that are classified, for example, as friends, family, and/or other close acquaintances.

Core attributes included in consumer avatar 600b may be shared with vendors and may include, for example, the user's address and payment information. It should be appreciated, however, that sub-avatars may be generated as needed by the registered users and data requesters. For example, a user may be associated with multiple consumer avatars, such as a mail-order consumer avatar to receive products to the user's home, a business consumer avatar to receive products to the user's workplace, and a personal services avatar to receive services at an appropriate location. Similarly, a sub-avatar may be associated with a particular vendor such that personal information required for a transaction with that vendor may be included in the avatar and available for access by the vendor. For example, a car rental company may require personal information (e.g., driver's license number, insurance policy number, age, etc.) that may not be needed by other types of vendors. To meet the specific needs, a vendor may provide information to the avatar data collection and access system 110 to define a sub-avatar that contains specific information.

Consumer avatar 600b may also include, for example, information regarding certain prior commercial activities by the user. For example, consumer avatar 600b may include information regarding prior purchases by the user but may omit information that could identify the user. In this way, consumer avatar 600b may be used to reliably collect commercial information from a customer without identifying the customer.

Employee avatar 600c may be shared, by data access interface component 340, with co-workers or an employer, and core attributes included in the employee avatar 600c may include, for example, the user's work address, work calendar, work contacts, education and work history, details, etc. Other information meaningful to an employer relationship may be included in employee avatar 600c. For example, employee avatar 600c may be used to share work-related information, such as identification of co-workers within a particular department, a status of a work project, or contact information for work associates and/or customers.

Data access interface component 340 may share healthcare avatar 600d with, for example, patients (when the user is identified as a healthcare provider) or a doctor (when the user is identified as a patient). The core attributes included in healthcare avatar 600d may include, for example, an indication of the user's role in healthcare (e.g., whether the user is a healthcare provider or a patient), healthcare information shared between the user and doctor, etc. For example, the healthcare avatar 600d may include information about the user's health or indicate a computer network address where this information can be acquired. Again, it should be appreciated that various sub-avatars may be defined as needed by the data requesters.

Also, while FIG. 6 depicts examples of avatars formed from user data, fewer avatars, different avatars, differently arranged avatars, and/or additional avatars than depicted in FIG. 6 may be used in implementations of the present application.

Figure 7:
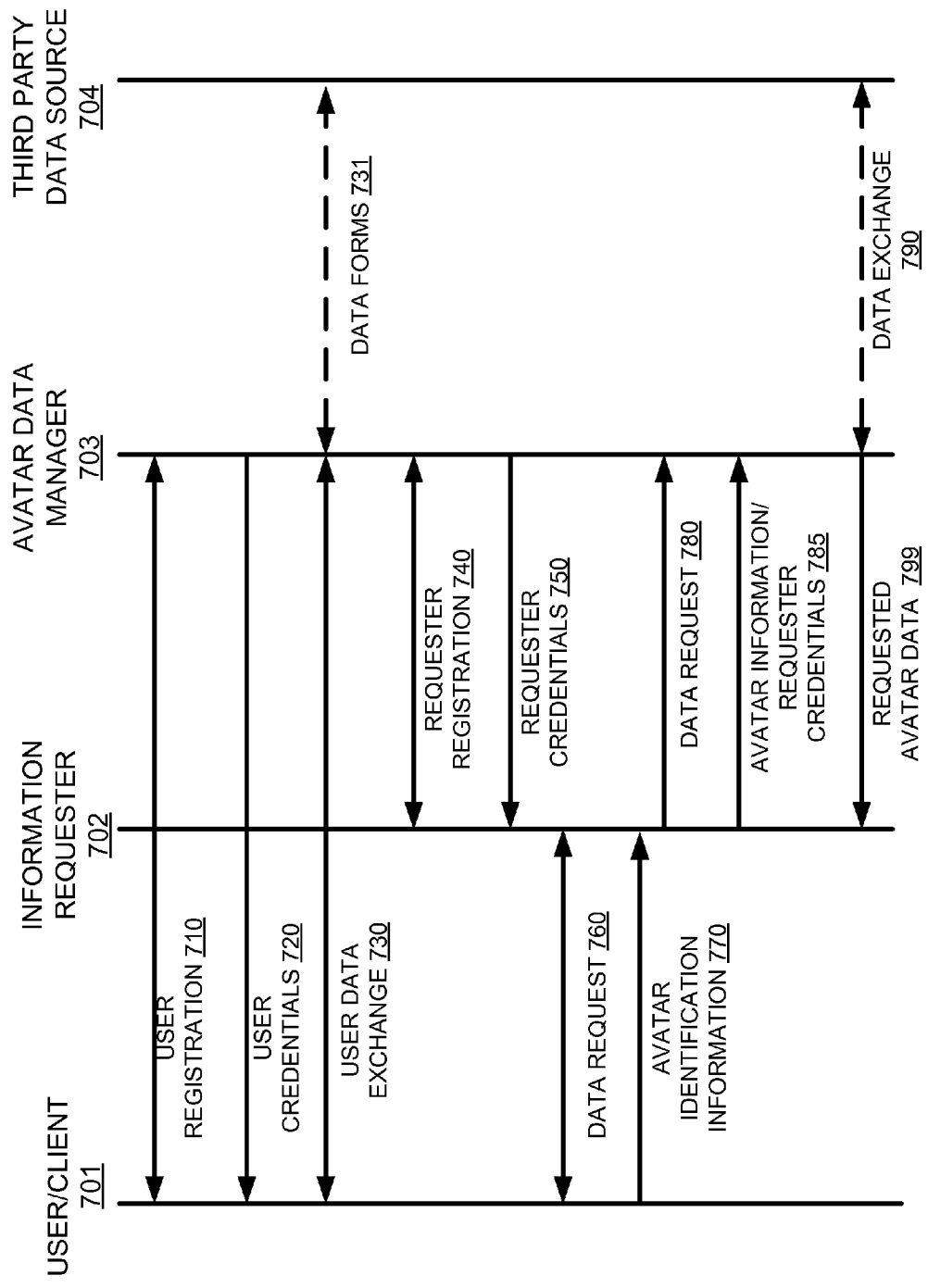
FIG. 7 is a diagram illustrating an example signal flow according to an implementation described herein.

FIG. 7 is a diagram illustrating an example of signal flows, according to an implementation described herein, that may be between one or more of user/client 701 (that may correspond to user device 120, information requester 702 (that may correspond to requesting devices 130), and avatar data manager 703 (that may correspond to avatar data collection and access system 110). According to an implementation described herein, the signal flows depicted in FIG. 7 may further include signals from third-party data source 704.

User/client 701 may exchange one or more user registration signals 710 with avatar data manager 703. For example, as described above with respect to user device 120, user registration signals 710 may include user/client 701 providing authentication data to avatar data manager 703, and avatar data manager 703 using this information to authenticate user/client 701.

Once authenticated, user/client 701 may receive user credentials signal 720 from avatar data manager 703. User credentials signal 720 may include credentials or encryption data that user/client 701 may use to authenticate information sent to avatar data manager 703. For example, user credentials signal 720 may include a digital signature or other known encryption key value that avatar data manager 703 may use to verify that information from user/client 701 is genuine and reliable.

For example, as part of personal data exchange signals 730, user/client 701 may receive one or more forms from avatar data manager 703, and provide the data requested in the received forms in a response to the avatar data manager 703. User/client 701 may use data provided in user credentials signal 720 to mark the reply data requested by the forms and included in one or more of personal data exchange signals 730. Avatar data manager 703, when receiving the reply to the form(s) from user/client 701, may use the data in user credentials signal 720 to authenticate the received data from user/client 701, such as to encrypt the data with an encryption code provided by avatar data manager 703 in user credentials signal 720.

One or more of the forms transmitted by avatar data manager 703 in personal data exchange signals 730 may optionally be received from data source 704 in data forms signal 731. For example, data source 704 may be an external data repository that stores and provides the forms. Alternatively, data source 704 may be associated with information requester 702.

Information requester 702 may exchange one or more requester registration signals 740 with avatar data manager 703. For example, avatar data manager 703 may request, through requester registration signals 740, information from information requester 702, and information requester 702 may provide this authentication data to avatar data manager 703. Avatar data manager 703 may use this information to authenticate information requester 702.

After registration through requester registration signals 740, avatar data manager 703 may provide requester credentials signal 750 to information requester 702. Requester credentials signal 750 may include credentials or encryption data that information requester 702 may use to authenticate another signal information sent to avatar data manager 703. For example, requester credentials signal 750 may include a digital signature or other known encryption data value that avatar data manager 703 may use to verify that other signals, such as a data request, from information requester 702 are genuine and reliable.

Continuing with FIG. 7, a series of signals for information requester 702 to acquire avatar information from avatar data manager 703 are now described. For example, data collection by information requester 702 may be initiated by data request signals 760 between user/client 701 and information requester 702. For example, as part of an on-line commercial transaction, user/client 701 may send an authorization and/or request to information requester 702 to initiate access to an avatar associated with user/client 701 and controlled by avatar data manager 703. Similarly, as part of a hospital registration, a patient associated with user/client 701 may authorize information requester 702 associated with the hospital to access the patient's medical records. As part of this authorization included in data request signals 760, user/client 701 may send avatar identification information signal 770 to information requester 702. For example, user/client 701 may send avatar identification information signal 770 to information requester 702 in exchange for some type of payment or service from information requester 702. Avatar identification information signal 770 may include data, such as an identifier associated with the avatar and/or additional authorization information, that information requester 702 may use to prove the authenticity of a related data request (data request signals 780) to avatar data manager 703.

For example, to access the data stored by avatar data manager 703, information requester 702 may send, with data request signals 780, avatar information/requester credentials signal 785 that may identify an avatar and may include credentials associated with information requester 702. For example, avatar information/requester credentials signal 785 may include the name of an avatar and/or credentials received from user/client 701 in avatar identification information signal 770. User/requester credentials signal 785 may further include credentials received by information requester 702 in requester credentials signals 750. Avatar data manager 703 may use the information in avatar information/requester credentials signal 785 to verify both that information access is authorized by user/client 701 and that information requester 702 is eligible to access the stored information. Similarly, as described above, avatar data manager 703 may determine whether to grant access to information based on one of user/client's avatars associated with the requested data and based on classification assigned to information requester 702.

Upon authentication of the information requester 702 based, for example, on user/requester credentials signal 785, avatar data manager 703 may locate the requested data. For example, avatar data manager 703, in one implementation, may locally store the information received from the user/client 701 in personal data exchange 730 and provide the requested avatar information based on this locally stored information. Avatar data manager 703 may optionally obtain the requested stored data from data source 704 (data exchange signal 790). Avatar data manager 703 may then send the requested data, through requested data signal 799, to information requester 702.

FIGS. 8A-8D are flow diagrams illustrating an avatar-based identity management process 800 according to an implementation described herein. In one implementation, avatar-based identity management process 800 may be performed by avatar data collection and access system 110. In other implementations, some or all of avatar-based identity management process 800 may be performed by another device or a group of devices separate from and/or possibly remote from avatar data collection and access system 110 and/or including avatar data collection and access system 110. In one implementation, avatar-based identity management process 800 may be manually initiated by an administrator. In another implementation, avatar-based identity management process 800 may be performed automatically (e.g., at particular intervals or in response to particular received data).

Figure 8A:
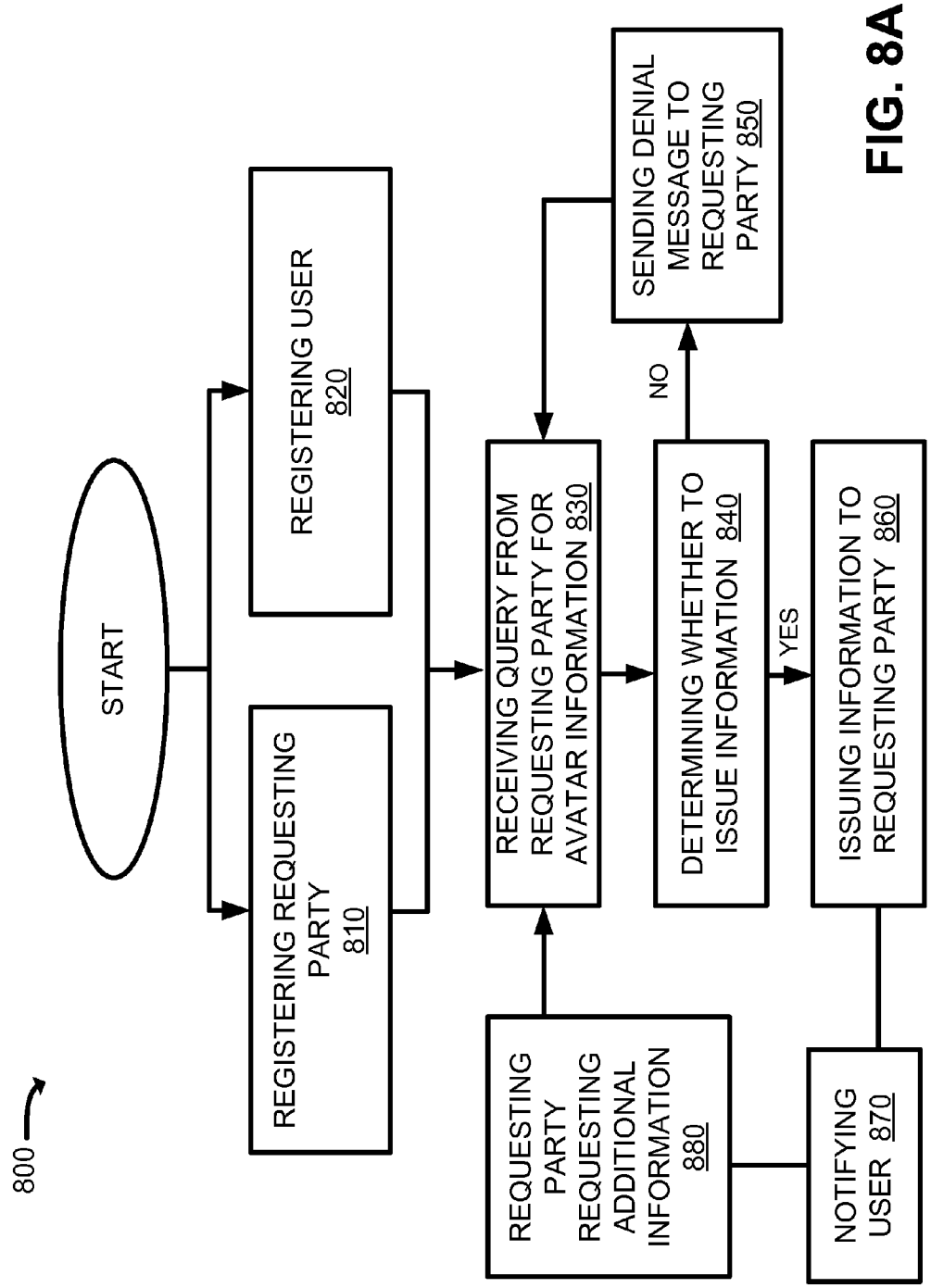
Figure 8B:
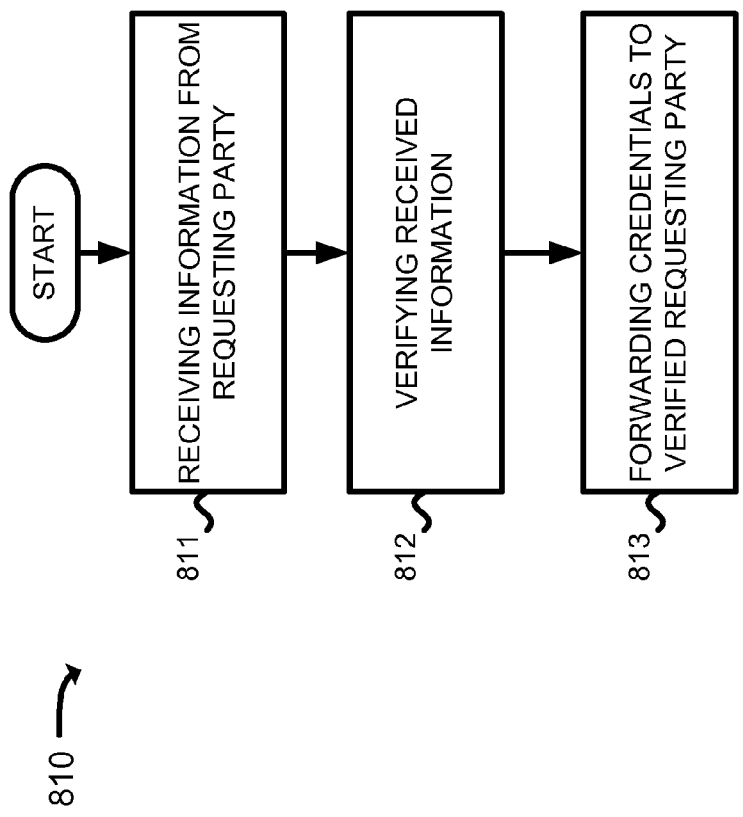

As depicted in FIG. 8A, avatar-based identity management process 800 may include registering of a requesting party, such as a user/entity associated with requesting device 130 (block 810). Process block 810 may include the process blocks depicted in FIG. 8B. As depicted in FIG. 8B, in one implementation, information may be received from the requesting party (block 811), and the requesting party may be verified based on the received information (block 812). For example, electronic verification of the received from the requesting party may be performed. It should be appreciated, however, that other known authentication techniques may be employed to verify the information received from the requesting party. Furthermore, credentials may be forwarded to the verified requesting party (block 813), and the forwarded credentials may include, for example, unique encryption codes or credentials to enable the verified requesting party to establish a secure session or other connection to request and access stored avatar-related information, as described below.

As depicted in FIG. 8A, avatar-based identity management process 800 may also include registering a user (block 820). Process block 820 may include the process blocks depicted in FIG. 8C. As depicted in FIG. 8C, in one implementation, registration information may be received from a user, such as a user associated with user device 120 (block 821). The user may be registered based on the received information (block 822). For example, the received information may identify the user, and this information may be verified to verify the user's identity. Various types of verifications may be used, such as electronic verification of the provided information. It should be appreciated, however, that other known verification techniques may be employed to verify the identity of the user.

Furthermore, credentials, such as unique encryption codes or credentials for establishing a secure session or other connection to, for example, avatar data collection and access system 110, may be provided to a verified user (block 823). For example, a personal identification number (PIN) may be assigned or, otherwise, an input from the user may be used to define a PIN. The credentials may be provided to a device associated with a registered user, such as user device 120, in the form of a cookie that operates through the associated device to identify the user to avatar data collection and access system 110.

Prior to accepting the data from the user, a verified user may be authenticated (block 824), such as to request that the user provide the PIN associated with the user. The user can be strongly authenticated by providing and/or verifying multiple types of personal information, such as to providing a PIN and additional personal information.

One or more forms may be provided to an authenticated and verified user (block 825) to collect data from the user. When the forms are provided to the verified and authenticated user, one or more fields in the forms may be pre-populated with previously collected and/or stored data associated with user, such as data acquired from other forms or the information provided by the user during registration. The personal information may be collected from the user (block 826), such as by collecting the user's response to the forms.

The data collected from the user may be organized to define one or more avatars (block 827). Information from the user's collected data may be associated with an avatar, for example, based on inputs from the user. Alternatively, or in addition, data from the user may into organized into avatars based on one or more forms from which the data was collected. Alternatively, or in addition, avatars are formed based on inputs received from a requesting party. For instance, a requesting party can specify data collected from the user, and the requested data may be included in an avatar available to the requesting party.

Although the above discussion describes data being received from a user with whom the data is associated, it should be appreciated that information can be received from a third party identified by the user. For example, the user, who is a patient, may request that information is collected from the user's doctor, who would receive and respond to the data request forms instead of the user.

Returning to FIG. 8A, avatar-based identity management process 800 may further include receiving a query from a requesting party to access avatar information that includes certain personal information collected from the user (block 830). In response to receiving the query, data access interface component 340 may determine whether to issue the information requested in the query (block 840).

Figure 8D:
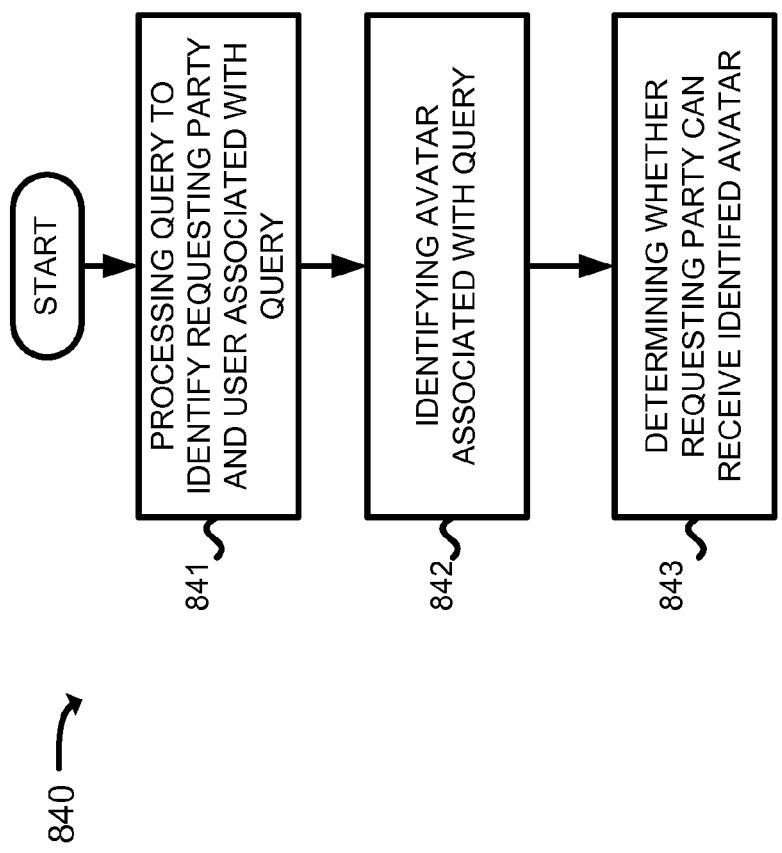

Process block 840 may include the process blocks depicted in FIG. 8D. Referring now to FIG. 8D, the query may be processed to identify a user and/or a requesting party associated with the query (block 841). For example, the requesting party may include, in the query, credentials associated with the data requester (e.g., assigned by data requester registration interface component 350) and/or the data provider (e.g., assigned by data provider registration interface component 320) to access one or more avatars. An avatar associated with the query may be identified (block 842). For example, an avatar may be identified by an identifier associated with the avatar (i.e., the avatar's name) or may be automatically determined based on processing a request from the data requester. A determination may be made regarding whether to provide the requested information based on identifying the requesting party and the identified avatar (block 843). For example, a user's "online transaction" avatar may be provided to an online vender, but that avatar may not be provided to another data requester.

In another implementation, the registered requesting party can access certain avatars without authorization from the user. For example, the requesting party can include a researcher who is collecting information about users without collecting information that could be used to identify the user. The requesting party collecting the anonymous information may include, for example, a researcher collecting information about the user's consumer behavior or information about the user's healthcare.

Continuing with FIG. 8A, if it is determined to deny the requesting party's query to access the requested information, such as when the requesting party's classification is not eligible to receive the user's avatar associated with the data included in the query, a denial message may be sent to the requesting party (block 850). The data providing user may provide instructions to modify the avatar or to modify access to the avatars, or the data requester may modify the query.

If it is determined to grant the requesting party's query to access the requested avatar (e.g., the requesting party is eligible to access the information associated with the requested avatar), the requested avatar may be issued to the requesting party (block 860). For example, where the avatar data includes a network address where information associated with the avatar is stored, issuing the requested avatar to the requesting party may include sending the network address to the data requester.

In one implementation, the registered user may be notified, for example, of access, by the requesting party, to the user's personal data contained in the accessed avatar (block 870). In response to accessing the information, the requesting party may update the query and/or request additional personal information from the user (block 880).

The foregoing description of implementations, described above, provides illustration and description, but is not intended to be exhaustive or to limit the implementations to the precise form disclosed. Modifications and variations are possible in light of the above teachings or may be acquired from practice of the invention.

For example, while series of blocks have been described with regard to FIGS. 8A-8D, the order of the blocks may be modified in other implementations. Further, non-dependent blocks may be performed in parallel.

Also, certain portions of the implementations may have been described as a "component" or "interface" that performs one or more functions. The terms "component" and "interface" may include hardware, such as a processor, an ASIC, or a FPGA, or a combination of hardware and software (e.g., software running on a processor).

It will be apparent that aspects described herein may be implemented in many different forms of software, firmware, and hardware in the implementations illustrated in the figures. The actual software code or specialized control hardware used to implement aspects does not limit the embodiments. Thus, the operation and behavior of the aspects were described without reference to the specific software code—it being understood that software and control hardware can be designed to implement the aspects based on the description herein.

Even though particular combinations of features are recited in the claims and/or disclosed in the specification, these combinations are not intended to limit the disclosure of the invention. In fact, many of these features may be combined in ways not specifically recited in the claims and/or disclosed in the specification.

No element, act, or instruction used in the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method, comprising:
   receiving, by a computer device, personal information associated with a user;
   removing, by the computer device, from the personal information a plurality of items of the personal information, wherein the plurality of items of the personal information comprises less than all items of the personal information;
   replacing, within the personal information, the plurality of items of the personal information with a plurality of items of information that are unrelated to the user to create replacement personal information associated with the user,
      wherein the plurality of items of information that are unrelated to the user comprise a plurality of items of personal information associated with a different user and wherein replacing the plurality of items of the personal information comprises swapping the plurality of items of the personal information associated with the user with the plurality of items of personal information associated with the different user, or
      wherein the plurality of items of information that are unrelated to the user comprise a randomly determined plurality of items of information that are unrelated to the user and wherein replacing the plurality of items of the personal information comprises replacing the plurality of items of the personal information with the randomly determined plurality of items of the information;
   verifying, by the computer device, one or more facts from the personal data;
   forming, by the computer device, an avatar based on the replacement personal information associated with the user;
   receiving information from a data requester;
   providing, to the data requester in response to receiving the information, an authentication code;
   receiving, by the computer device and from the data requester, a query including a request for the avatar; and
   determining whether the query further includes the authentication code;
   sending, by the computer device and to the data requester, a message that includes:
      information associated with the avatar, and
      an indication that the one or more facts from the personal information are verified,
      wherein sending the message is in response to determining that the query includes the authentication code.

2. The method of claim 1, further comprising:
   forming a plurality of avatars based on the personal information associated with the user; and
   selecting one of the plurality of avatars based on the query.

3. The method of claim 2, further comprising:
   sending, to the user, one or more forms requesting the personal information associated with the user.

4. The method of claim 3, wherein each of the one or more forms is associated with at least one of the plurality of avatars.

5. The method of claim 3, wherein one form, of the one or more forms, is sent to the computer device by the data requester.

6. The method of claim 1, further comprising:
   receiving information from the data requester; and
   determining whether to send the message to the data requester based on the information received from the data requester.

7. A device, comprising:
   a memory to store instructions; and
   a processor to execute the instructions to:
      receive personal information associated with a user,
      remove, from the personal information, a plurality of items of the personal information, wherein the plurality of items of the personal information comprises less than all items of the personal information,
      replace, within the personal information, the plurality of items of the personal information with a plurality of items of information that are unrelated to the user to create replacement personal information associated with the user,
         wherein the plurality of items of information that are unrelated to the user comprise a randomly determined plurality of items of information that are unrelated to the user and wherein replacing the plurality of items of the information comprises replacing the plurality of items of the personal information with the randomly determined plurality of items of the information,
      form an avatar based on the replacement personal information associated with the user,
      receive information from a data requester,
      provide, to the data requester in response to receiving the information, an authentication code,
      receive, from the data requester, a query including a request for the avatar,
      determine whether the query further includes the authentication code, and
      send, to the data requester, a message that includes information associated with the avatar, wherein sending the message is in response to determining that the query includes the authentication code.

8. The device of claim 7, wherein the processor is further configured to:
   form a plurality of avatars based on the personal information associated with the user; and
   select one of the plurality of avatars based on the query.

9. The device of claim 8, wherein the processor is further configured to:
   send, to the user, one or more forms requesting the personal information associated with the user.

10. The device of claim 9, wherein each of the one or more forms is associated with at least one of the plurality of avatars.

11. The device of claim 9, wherein one form, of the one or more forms, is received by the device from the data requester.

12. The device of claim 7, wherein the processor is further configured to:
- receive information from the data requester; and
- determine whether to send the message to the data requester based on the information received from the data requester.

13. A tangible non-transitory computer-readable medium storing instructions executable by a processor, the tangible non-transitory computer-readable medium comprising:
- one or more instructions for receiving personal information associated with a user;
- one or more instructions for removing, from the personal information, a plurality of items of the personal information, wherein the plurality of items of the personal information comprises less than all items of the personal information;
- one or more instructions for replacing, within the personal information, the plurality of items of the personal information with a plurality of items of information that are unrelated to the user to create replacement personal information associated with the user,
  - wherein the plurality of items of information that are unrelated to the user comprise a plurality of items of personal information associated with a different user and wherein replacing the plurality of items of the personal information comprises swapping the plurality of items of the personal information associated with the user with the plurality of items of personal information associated with the different user;
- one or more instructions for forming an avatar based on the replacement personal information;
- one or more instructions for receiving information from a data requester;
- one or more instructions for providing, to the data requester in response to receiving the information, an authentication code;
- one or more instructions for receiving, from a data requester, a query including a request for the avatar;
- one or more instructions for determining whether the query further includes the authentication code;
- one or more instructions for sending, to the data requester, a message that includes information associated with the avatar,
- wherein sending the message is in response to determining that the query includes the authentication code.

14. The tangible non-transitory computer-readable medium of claim 13, further comprising:
- one or more instructions for forming a plurality of avatars based on the personal information associated with the user; and
- selecting one of the plurality of avatars based on the query.

15. The tangible non-transitory computer-readable medium of claim 14, further comprising:
- one or more instructions for sending, to the user, one or more forms requesting the personal information associated with the user.

16. The tangible non-transitory computer-readable medium of claim 15, wherein each of the one or more forms is associated with at least one of the plurality of avatars.

17. The tangible non-transitory computer-readable medium of claim 13, further comprising:
- one or more instructions for receiving information from the data requester; and
- one or more instructions for determining whether to send the message to the data requester based on the information received from the data requester.

* * * * *